United States Patent
Leach et al.

(10) Patent No.: US 8,748,600 B2
(45) Date of Patent: *Jun. 10, 2014

(54) CYCLIC TRIAZO SODIUM CHANNEL BLOCKERS

(75) Inventors: Michael Leach, Chatham Kent (GB); Karl Franzmann, Chatham Kent (GB); Dieter Riddall, Chatham Kent (GB); Laurence Harbige, Chatham Kent (GB)

(73) Assignee: University of Greenwich, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/382,741

(22) PCT Filed: Jul. 8, 2010

(86) PCT No.: PCT/GB2010/051127
§ 371 (c)(1),
(2), (4) Date: Feb. 14, 2012

(87) PCT Pub. No.: WO2011/004196
PCT Pub. Date: Jan. 13, 2011

(65) Prior Publication Data
US 2012/0135993 A1     May 31, 2012

(30) Foreign Application Priority Data
Jul. 8, 2009  (GB) .................... 0911993.4

(51) Int. Cl.
*C07D 253/07* (2006.01)
*A61K 31/53* (2006.01)
*A61P 25/08* (2006.01)
*A61P 25/28* (2006.01)
*A61P 25/04* (2006.01)

(52) U.S. Cl.
USPC .......................................... 544/182; 514/242

(58) Field of Classification Search
USPC .................. 544/182, 242, 183; 514/242
See application file for complete search history.

(56) References Cited

U.S. PATENT DOCUMENTS

| | | | |
|---|---|---|---|
| 3,637,688 A | 1/1972 | Rees et al. | |
| 8,268,823 B2 * | 9/2012 | Leach et al. | 514/242 |

FOREIGN PATENT DOCUMENTS

| | | |
|---|---|---|
| EP | 0 021 121 A1 | 1/1981 |
| WO | WO2008/007149 | 1/2008 |
| WO | WO2009/090431 | 7/2009 |

OTHER PUBLICATIONS

Krafte et al., Current Opinion in Pharmacology 2008, 8:50-56.*
Rush et al., Molecular Interventions 2007, vol. 4, issue 7, 192-195.*
Dermer et al., Bio/Technology, 1994, 12:320.*
Freshney et al.,Culture of Animal Cells, A Manual of Basic Technique, Alan R. Liss, Inc., 1983, New York, p. 4.*
Clare et al, Drug Discovery Today 2000, vol. 5, No. 11,506-520.*
Cecil Textbook of Medicine, edited by Bennet, J.C., and Plum F., 20th edition,vol. 1, 1004-101 O, 1996.*
Golub et al., Science, 286, 531-537, 1999.*
Mass, R. D., Int. J. Radiation Oncology Bio. Phys. vol. 58(3): 932-940, 2004.*
Fabbro et al. Pharmacology & therapeutics 93, 79-98, 2002.*
Limanto et al., "A regioselective approach to 5-substituted-3-amino-1, 2, 4-triazines" ORG. LETT., vol. 5, No. 13, Jun. 26, 2003.
Rees, et al., "Antimalarial Activities of Some 3,5-Diamino-as-Triazine Derivatives", J. MED. CHEM., vol. 15, No. 8, Jan. 1, 1972, pp. 859-861.

* cited by examiner

*Primary Examiner* — Venkataraman Balasubramanian
(74) *Attorney, Agent, or Firm* — Cesari and McKenna, LLP

(57) ABSTRACT

The present invention relates to triazine compounds having sodium channel blocking properties, and to use of the compounds for preparation of medicaments for treatment of associated disorders. The triazine compounds are of formula (I) wherein: R1 is hydrogen or a substituent group; R2 is amino or a substituent group; N* is amino when R1 is hydrogen or =NH when R1 is a substituent group; R3 and R4 are both carbocyclic, heterocyclic or alkyl groups and may be same or different; and R5 is hydrogen, alkyl or a cyclic aryl group, with the proviso that: when R3 and R4 are both alkyl they are linked to form a cycloalkyl group, and R5 is a cyclic aromatic group; and when R3 and R4 are both carbocyclic or heterocyclic groups, R5 is hydrogen or an alkyl group; or a salt thereof.

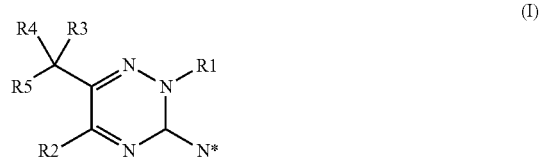

(I)

24 Claims, No Drawings

CYCLIC TRIAZO SODIUM CHANNEL BLOCKERS

CROSS-REFERENCE TO RELATED APPLICATIONS

This application is the National Stage of International Application No. PCT/GB2010/051127, filed on Jul. 8, 2010, which claims the priority date of United Kingdom Application No. 0911993.4, filed on Jul. 8, 2009 the contents of which is being hereby incorporated by reference in its entirety.

The present invention relates to triazine compounds having sodium channel blocking properties, and to use of the compounds for preparation of medicaments for treatment of associated disorders.

U.S. Pat. No. 4,649,139 discloses compounds of the formula (A):

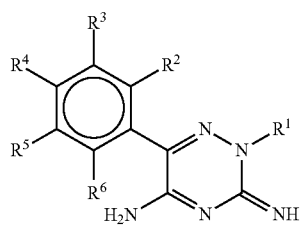

(A)

in which $R^1$ is $C_{1-10}$ alkyl, $C_{2-10}$ alkenyl, $C_{2-10}$ alkynyl or $C_{3-10}$ cycloalkyl, any of which is optionally substituted, and $R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups or any adjacent two of $R^2$ to $R^6$ are linked to form a (—CH═CH—CH═CH—) group. It is disclosed that these compounds are active in the treatment of cardiac disorders, and are particularly useful in the treatment of arrhythmias.

Our previous patent application WO2008/007149 discloses uses of a compound of formula (B):

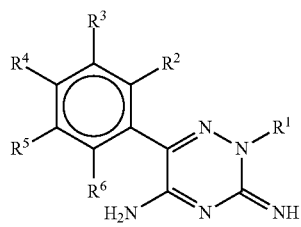

(B)

in which $R^1$ is hydrogen (and ═NH is $NH_2$), or carboxamido, $C_{1-10}$ alkyl, $C_{2-10}$ alkenyl, $C_{1-3}$ alkyl-aryl, $C_{1-3}$ alkyl-heterocyclyl, or $C_{3-10}$ cycloalkyl, any of which is optionally substituted by hydroxy, halogen, carboxamido, halo $C_{1-6}$ alkyl, $C_{1-6}$ alkyl or $C_{1-6}$ alkoxy; and $R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups;

(a) as voltage dependent sodium channel blockers for the treatment of disorders in mammals, and particularly epilepsy, multiple sclerosis, glaucoma and uevitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias, especially in humans;

(b) as antifolates for the treatment of disorders in mammals, and particularly for treatment of mammalian cancers and as antimalarials against *plasmodium vivax* and *plasmodium falciparum* malaria, especially in humans.

The present invention provides compounds of formula (I)

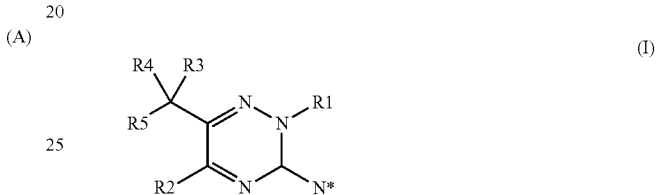

(I)

in which
$R^1$ is hydrogen or a substituent group;
$R^2$ is amino or a substituent group;
N* is amino when $R^1$ is hydrogen or ═NH when R1 is a substituent group;
R3 and R4 are both carbocyclic, heterocyclic or alkyl groups; and
R5 is hydrogen, alkyl or a cyclic aryl group, with the proviso that: when R3 and R4 are both alkyl they are linked to form a cycloalkyl group, and R5 is an aromatic or cyclic aliphatic group; and when R3 and R4 are both carbocyclic or heterocyclic groups, R5 is hydrogen, an alkyl group or an aromatic group.

Preferably, R3 and R4 are aromatic carbocycles or aromatic heterocycles, and R5 is hydrogen.

Suitably, R3 and R4 are both alkyl and linked to form a cyclopropyl, cyclobutyl, cyclopentyl or cyclohexyl group.

Suitably R3, R4 or R5 are selected from methyl, ethyl, propyl and butyl, optionally substituted, for example, by halogen or alkoxy groups.

Optionally, R1 is carboxamido, $C_{1-10}$ alkyl, $C_{2-10}$ alkenyl, $C_{1-3}$ alkyl-aryl, $C_{1-3}$ alkyl-heterocyclyl, or $C_{3-10}$ cycloalkyl, any of which is optionally substituted by hydroxy, halogen, carboxamido, halo $C_{1-6}$ alkyl, $C_{1-6}$ alkyl or $C_{1-6}$ alkoxy.

Suitably, R1 is an unsubstituted $C_{1-6}$ alkyl group, typically methyl, ethyl, i-propyl, n-propyl, i-butyl or n-butyl, optionally substituted by hydroxy or halogen, such as chloro, bromo or fluoro.

Alternatively, R1 is $C_{1-10}$ halo-alkyl, preferably methyl, ethyl, i-propyl, n-propyl, i-butyl or n-butyl, substituted by one or more halogens, such as chloro, bromo or fluoro. Preferred substitutions are di- or tri-halo (especially chloro and/or fluoro).

Alternatively R1 is an unsubstituted $C_{2-6}$ alkenyl group, such as allyl; a $C_{3-10}$ cycloalkyl group, such as cyclohexyl; a $C_{1-3}$ alkylaryl group, such as benzyl; optionally substituted by one or more halogen, haloalkyl or alkoxy groups, for example chloro, fluoro, trifluoromethyl, trifluoromethoxy, methoxy or ethoxy.

Alternatively, R1 is a $C_{1-3}$ alkyl-heterocyclyl group such as piperidine-methyl, optionally N-substituted, or thienyl-methyl, or furyl-methyl.

Typically, one or more of R3, R4 and R5 is a carbocyclic ring system, such as phenyl. Optional substituents of R3, R4 and R5 may be present, such as halogens (chloro, fluoro, bromo) and alkoxy, for example methoxy.

In group compounds of formula (I) at least one of R3, R4 and R5 is an heterocyclic ring system, for example a monocyclic or bicyclic heterocycle with one or more oxygen or sulphur or nitrogen atoms, especially an aromatic heterocyclic ring system. In preferred embodiments R3=R4.

Suitably, the heterocyclic group is (i) a sulphur-containing heterocycle selected from thienyl and benzothienyl groups; (ii) an oxygen-containing heterocycle selected from furyl, phenylfuryl and benzopyranyl; or a nitrogen-containing heterocycle selected from pyridyl, indolyl, quinolyl and isoquinolyl. Advantageously, substituted as for the structures described above; for carbocyclic A rings, for example by halogen, alkyl or alkoxy, especially by 1, 2 or 3 chlorine or bromine atoms. Nitrogen-containing heterocycles are optionally N-substituted by alkyl such as methyl, or substituted by phenoxy or phenylthio, with the phenyl optionally substituted by halogen such as chloro.

The present invention also provides salts of any of the above compounds. Preferred salts are pharmaceutically acceptable acid addition salts. Suitable pharmaceutically acceptable acid addition salts include those formed with both organic and inorganic acids, for example from hydrochloric, sulphuric, citric, tartaric, phosphoric, lactic, pyruvic, acetic, malonic, succinic, oxalic, fumaric, maleic, oxaloacetic, methanesulphonic, p-toluenesulphonic, benzene-sulphonic, glutamic, naphthoic, and isethionic acids. Ethanesulphonate, malate, mandalate, benzoate, and salicylate salts are also suitable.

The present invention also provides solvates of any of the compounds of formula (I) or salts thereof. The compound or its salt may be obtained as a solvate of the reaction solvent or crystallisation solvent or a component thereof in preparation of the compound. Suitable pharmaceutically acceptable solvates include hydrates.

Compounds of formula (I) may have chiral centres and may occur as racemates, racemic mixtures and as individual enantiomers or diastereomers. All such isomeric forms are included within the present invention. Also included within the scope of the invention are all geometric isomers of the compound of formula (I) whether as individual isomers or mixtures thereof. Thus compounds of formula (I) in the trans- and cis-configuration are encompassed by the present invention; as are tautomeric forms and mixtures thereof, and polymorphic crystalline forms.

Certain compounds of formula (I) may be prepared by the procedures disclosed in the above-mentioned U.S. Pat. No. 4,649,139, the entire disclosure of which is incorporated herein by reference and to which further reference should be made. Certain compounds of formula (I) may also be prepared by methods disclosed in EP 0 021 121 A, the entire disclosure of which is incorporated herein by reference and to which further reference should be made.

The preparation of specific compounds mentioned above is illustrated later in this specification. Related compounds within the scope of the invention may be prepared by obvious or routine variations of the disclosed processes, using appropriate starting materials to introduce the desired substituents and moieties of compounds within the scope of formula (I).

Salts of compounds of formula (I) may be obtained by the presence of a residual acid in the preparative process. Alternatively salts may be prepared by mixing the compound of formula (I) as the free base with a pharmaceutically acceptable acid in a suitable solvent, and removing the solvent to recover the salt, or crystallising the salt from the solvent.

In a further aspect, the present invention provides pharmaceutical compositions comprising a compound of formula (I) or a pharmaceutically acceptable salt or solvate thereof, in admixture with a pharmaceutically acceptable carrier. The compounds are suitable for the treatment of disorders such as epilepsy, multiple sclerosis, glaucoma and uevitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

The compounds of formula (I) are present in the compositions of the present invention in an effective unit dosage form, that is to say in an amount sufficient to be effective against the disorders in vivo.

The pharmaceutically acceptable carriers present in the compositions of the present invention may be materials conventionally used for the purpose of administering the medicament. These may be liquid or solid materials, which are otherwise inert or medically acceptable and are compatible with the active ingredients.

These pharmaceutical compositions may be given orally or parenterally, for example as a suppository, ointment, cream, powder or trans-dermal patch. However, oral administration and intravenous injection of the compositions are preferred.

For oral administration, fine powders or granules will contain diluting, dispersing and/or surface active agents, and may be presented in draught, in water or in a syrup, in capsules or sachets in the dry state or in non-aqueous suspension wherein suspending agents may be included, or in a suspension in water or syrup. Where desirable or necessary, flavouring, preserving, suspending, or thickening agents can be included. Dry powders or granules may be compressed to form a tablet or contained in a capsule.

For injection, the compounds may be presented in sterile aqueous injection solutions which may contain anti-oxidants or buffers.

The free base or a salt or solvate thereof may also be administered in its pure form unassociated with other additives in which case a capsule or sachet is the preferred carrier.

Alternatively the active compound is presented in a pure form at an effective unit dosage, for instance compressed as a tablet or the like.

Other compounds which may be included are, for example, medically inert ingredients, e.g., solid and liquid diluents such as lactose, starch, or calcium phosphate for tablet or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Tablets or other forms of presentation provided in discrete units may conveniently contain an amount of compound of formula I which is effective at such dosage or as a multiple of the same, for instance units containing 5 mg to 500 mg, usually around 10 mg to 250 mg.

The pharmaceutical compositions of the present invention may be prepared by the admixture of a compound of formula (I) with a pharmaceutically acceptable carrier. Conventional pharmaceutical excipients may be admixed as required. Example of suitable formulations are give in the above-mentioned U.S. Pat. No. 4,649,139.

The present invention provides a method of treatment by the administration of a non-toxic effective amount of a compound of formula (I) or a pharmaceutically acceptable salt or solvate thereof, or a composition as hereinbefore defined. The method is particularly suitable for the treatment of disorders in mammals that are susceptible to sodium channel blockers and antifolates, and particularly disorders such epilepsy, multiple sclerosis, glaucoma and uevitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

The present invention also provides a compound of formula (I) or a pharmaceutically acceptable salt or solvate thereof, or a composition as hereinbefore defined for, or for the preparation of a medicament. The medicament is particularly suitable for treatment of disorders in mammals that are susceptible to sodium channel blockers and antifolates, and particularly disorders such epilepsy, multiple sclerosis, glaucoma and uevitis, cerebral traumas and cerebral ischaemias, stroke, head injury, spinal cord injury, surgical trauma, neurodegenerative disorders, motorneurone disease, Alzheimer's disease, Parkinson's disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

As indicated above, the compounds of formula (VI) are generally useful in treating such disorders by oral administration or intravenous injection.

The compounds of formula (I) are normally administered at a dose of from 0.01 mg/kg to 20 mg/kg per day, preferably 0.1 to 5.0 mg/kg per day.

In view of the known use in humans of structurally similar compounds such as lamotrigine, and other known compounds within the scope of formula (I), no major toxicity problems are anticipated in use of compounds of formula (I). However appropriate testing procedures should be carried out before clinical use.

The above and other aspects of the present invention will now be illustrated in further detail with reference to the accompanying examples.

The methodology for preparation of illustrative compounds of formula (I) and other compounds used in testing, is reported below. This may be adapted to prepare analogous compounds with additional or alternative substituents or moieties mentioned herein.

In the procedures below all temperatures are in ° C.

General Procedure

6-Alkyl/Aralkyl-3,5-diamino-1,2,4-triazine compounds

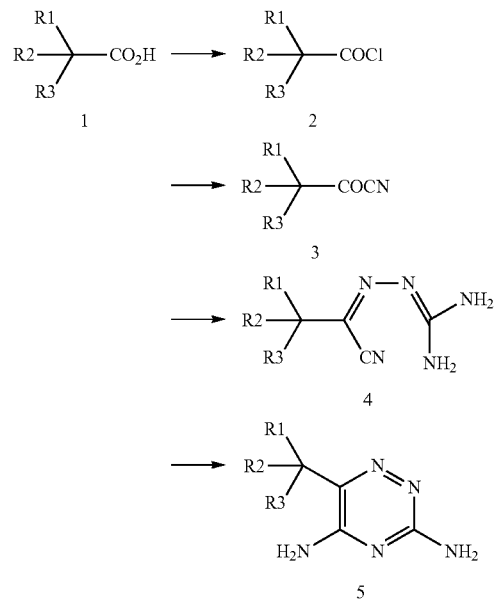

Triphenylacetyl chloride [3; $R_1=R_2=R_3=Ph$]

A stirred mixture of triphenylacetic acid (21.7 g; 0.075 mol) and dry dimethylformamide (2 drops) in dry dichloromethane (100 cm$^3$) was treated with oxalyl chloride (14 g; 0.11 mol) which was added in 4 approximately equal portions over ~25 minutes. The mixture was stirred at 35° until evolution of hydrogen chloride had ceased (~4 hrs). The resulting colourless solution was evaporated in vacuo at 40° to constant weight to give the title compound as a colourless crystalline solid. Yield=23.24 g (100.0%). The product was used directly in next stage.

Similarly prepared were:

Triphenylacetyl cyanide [4; $R_1=R_2=R_3=Ph$]

A well stirred mixture [paddle stirrer] of triphenylacetyl cyanide (23.24 g; 0.075 mol), dry toluene (40 cm$^3$), dry acetonitrile (10 cm$^3$), copper I cyanide (9.20 g; 0.103 mol), Celite (3.5 g) and finely powdered potassium iodide (2 g) was heated under reflux until no acid chloride remained (~18 hrs). The dark reaction mixture was cooled to ~75° and diluted with toluene (150 cm$^3$). After stirring for an additional ~30 minutes, the resulting slurry was filtered through a bed of chromatographic silica gel (~2.5 cm) and the colourless filtrate evaporated in vacuo to constant weight to give the title compound as a colourless solid. Yield=21.97 g (98.7%), Mpt=67-69°. The product was used directly in next stage.

Schiffs Base, cyanohydrazone, (4; $R_1=R_2=R_3=Ph$]

To a stirred solution of aminoguanidine bismesylate (15.00 g; 0.0564 mol) in 99.5% methanesulphonic acid (22.5 g) at 65-70° was added dropwise a solution of Triphenylacetyl cyanide (8.91 g; 0.030 mol) in acetonitrile (25 cm³) over ~25 minutes. The mixture was then stirred at 68° until a sample gave a clear solution in water (~28 hrs) and then poured onto crushed ice/water (150 g) giving a semi-solid colourless precipitate. The mixture was neutralised (pH 8-9) with 48% sodium hydroxide (17.5 cm³) giving the title compound as cream granular solid. The product was filtered off, washed with water and dried in vacuo at 45°. Yield=8.47 g (80.0%), Mpt=112-114°, TLC [SiO₂ plate, 10% methanol in chloroform], $R_f$=0.68. The product was used directly in the next stage.

Triazine Compounds

CEN-230

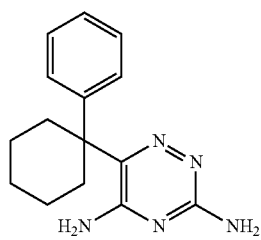

CEN-231

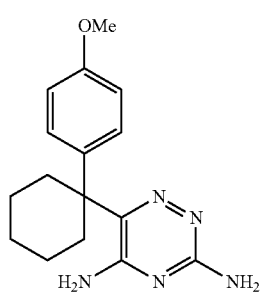

CEN-232

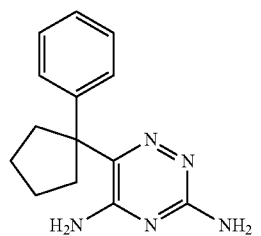

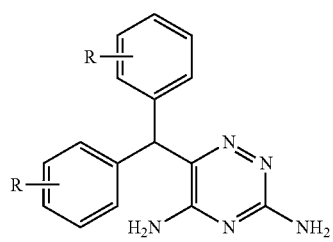
R = 4-Cl
= 4-OMe
= 4-F
= 4-CF₃

-continued

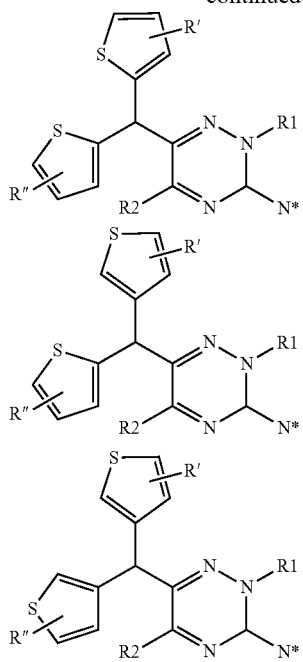

CEN234

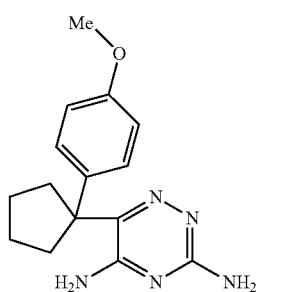

CEN235

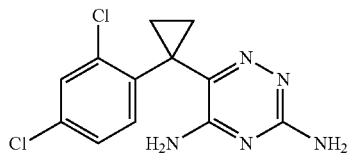

CEN236

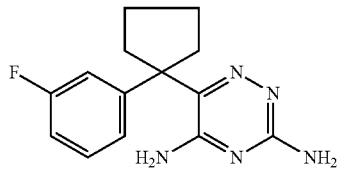

CEN237

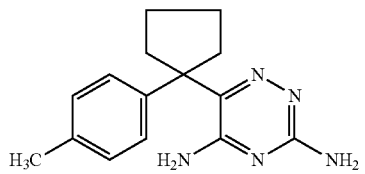

CEN238

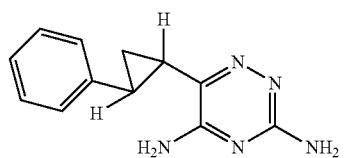

CEN239
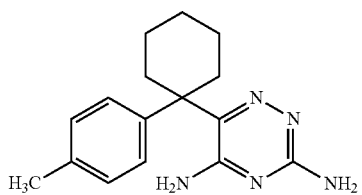

CEN240
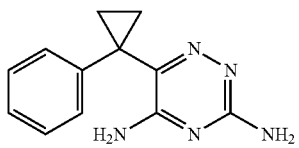

CEN241
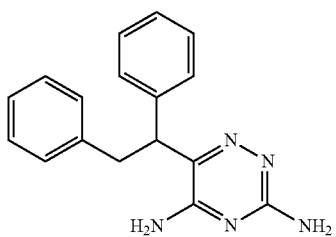

CEN244
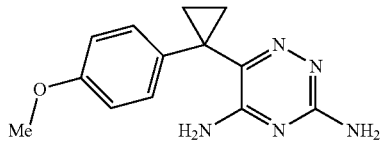

CEN245
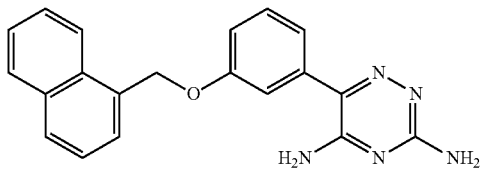

CEN247
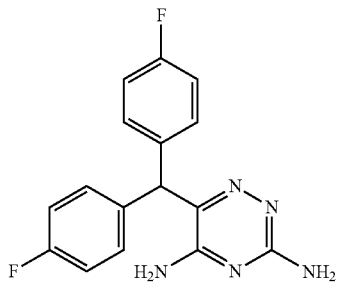

Biological Testing

Compounds of Formula (VII) were tested for various activities as follows:

Screening Strategy

The screening strategy is designed to select compounds with appropriate sodium channel blocking activity and low side effect liability. To this end all compounds are processed through the primary sodium channel assay (veratrine-evoked uptake of [$^{14}$C]guanidine into rat forebrain synaptosomes) and $IC_{50}$ values computed from generated concentration-effect curves. In order to complement this data $IC_{50}$'s for selected compounds to inhibit binding of [$^3$H]BTX-B are also measured.

Previous studies have shown that substituted triazines are potential inhibitors of DiHydroFolate Reductase (DHFR) activity (McCullough and Bertino 1971, Cashmore et al, 1975, Booth et al, 1987) and Sapse et al, 1994). Inhibitors of DHFR (such as Methotrexate) have been used for the treatment of various cancers (Suster et al, 1978 and Niculescu-Duvaz et al, 1982) as inhibition of this enzyme interferes with cell growth but because of this effect (on cell growth) inhibitors of DHFR may also be teratogenic (Skalko and Gold, 1974, Feldcamp and Carey, 1993 and Buckley et al, 1997). Should compounds be found which are potent inhibitors of DHFR then such compounds may, themselves, have potential as anti-cancer agents. Several methods are available for measurement of inhibition of DHFR activity and for this study we have examined effects of compounds to inhibit the binding of [$^3$H] methotrexate (Myers et al, 1975 and Rothenberg et al, 1977).

Another common side-effect marker is inhibition of human Ether-a-go-go Related Gene potassium (hERG) potassium channel (Inward rectifying, $I_{Kr}$) activity which can be fatal due to heart failure brought about by development of long QT syndrome. A useful preliminary screen to assess potential to affect this channel is assessed by measurement of inhibition of the binding of [3H]astemizole to cell membranes expressing hERG. Selected compounds are tested for this activity by measurement of inhibition @ 10 µM. Assuming inhibition values lie between 10% and 90% it is possible to compute an extrapolated $IC_{50}$ for each compound.

The above screening cascade identifies compounds with appropriate sodium channel blocking activities that have a low(er) propensity for aforementioned side-effect liabilities. In order to develop these compounds further, some knowledge of their pharmacodynamic properties is required.

Sodium channel blockers, such as Sipatrigine, which both reduces the neurological deficit and infarct volume after middle cerebral artery occlusion in rats (Smith et al, 1997) and phenyloin, (which protect retinal ganglion cell death in an experimental model of glaucoma (Hains and Waxman, 2005) show neuroprotective efficacy in a range of models of nerve degeneration. As failure of oxygen supply compromises both glycolysis and oxidative phosphorylation, ischaemic damage ultimately leads to electrical failure (nerve signalling) and pump failure (restoration of cellular membrane potentials). These failures (of electrical and ion pump activity) are associated with decreased local concentrations of ATP (Astrup et al 1981). Thus the effect of compounds to maintain concentrations of ATP in 0.4 mm slices of rat hippocampus following a severe metabolic insult was used.

EXPERIMENTAL PROCEDURES

Preparation of Rat Forebrain Synaptosomes and Homogenates

Experiments were performed using forebrain (whole brain less cerebellum/medulla) from Male Wistar rats weighing 175-250 g. All efforts were made to reduce the number of animals used and all experiments were carried out in accordance with the UK Animals (Scientific Procedures) Act, 1986 and the European Community Council Directive of 24 Nov. 1986 (86/609/EEC). Following killing of animals by stunning and decapitation, the forebrain (whole brain less cerebellum/medulla) was rapidly dissected and transferred to a weighed tube containing ice-cold 0.25M sucrose.

Synaptosomes (heavy and light mitochondrial fraction containing synaptosomes) were prepared by transferring the forebrain (of known wet weight) to a glass Potter vessel to which 9 volumes ice-cold 0.25M sucrose had been added and homogenising, using a teflon pestle, by 8 'up and down strokes' of a Braun Potter S motor driven homogeniser set to 900 rpm. The resulting homogenate was centrifuged at 1036×g at 4° for 10 min and the supernatant collected. The remaining pellet was resuspended, as above, in fresh ice-cold 0.25M sucrose and the centrifugation step repeated. The supernatant fractions were pooled and centrifuged at 40,000×g (average) at 4° for 15 min and the resulting pellet resuspended in the appropriate assay buffer at a concentration of 20-25 mg wet weight per ml appropriate assay buffer.

Homogenates were prepared by transferring the known weight of forebrain to a cooled tube containing 9 volumes of ice-cold 50 mM pH 7.4 HEPES buffer. The mixture was homogenised @ 4° by 3×5 sec bursts of an Ultra-Turrax™ homogeniser set at maximum speed. The resulting homogenate was centrifuged at 40,000×g (average) at 4° for 15 min and the supernatant discarded. The resulting pellet was resuspended in 9 volumes of fresh ice-cold pH 7.4 buffer (as above), the centrifugation step was repeated and the resulting pellet resuspended in the [$^3$H]BTX-B binding buffer at a concentration of 20-25 mg wet weight per ml assay buffer.

[$^{14}$C] Guanidine Flux and Binding of [$^3$H]BTX-B

Both assays were carried out using 14 ml polypropylene test tubes to which a range of concentrations of the compounds under test were added. Test compounds were dissolved in DMSO and added to assays such that maximum concentration of DMSO did not exceed 2% v/v.

[$^{14}$C]Guanidine Flux:

The [$^{14}$C] guanidinine flux assay was measured using the method of Pauwels P J et al (1986) but carried out @ 30° for 2% min.

REFERENCES

Pauwels P J, Leysen J E, Laduron P M. [3H]Batrachotoxinin A 20-alpha-benzoate binding to sodium channels in rat brain: characterization and pharmacological significance. Eur J. Pharmacol. 1986 May 27; 124(3):291-8.

Binding of [$^3$H]BTX-B

[$^3$H]BTX-B binding was carried out using the method described by Catterall et al (1981), except that both bovine serum albumin and TTX were omitted from the incubation medium. Test compounds were dissolved in DMSO and added to assays such that maximum concentration of DMSO did not exceed 2% v/v.

REFERENCES

Catterall W A, Morrow C S, Daly J W, Brown G B. Binding of batrachotoxinin A 20-alpha-benzoate to a receptor site associated with sodium channels in synaptic nerve ending particles. J. Bio. Chem. 1981 Sep. 10; 256(17): 8922-7.

Binding of [$^3$H]Methotrexate

All steps were carried out at 4° (or on ice). Freshly dissected rat liver was dissected into 0.25M ice-cold Sucrose and subsequently homogenised (U-turrax) in 50 mM pH 6.0 phosphate buffer (10 ml/g tissue) containing 15 mM Dithiothreitol. The resulting homogenate was centrifuged @ 47,500×g for 20 min and supernatant (filtered through cotton wool to remove fatty lumps) stored @-80° before use (Rothenberg et al).

Inhibition of the binding of [$^3$H]methotrexate to rat liver homogenate supernatant fractions were carried out essentially as described by Arons et al, 1975. Results were calculated, either as IC$_{50}$ values (see below) derived from concentration-effect curves or as percentage inhibition values determined by comparison with control and cold Methotrexate (10 μM final concentration) binding values.

References:

Elliot Arons, Sheldon P. Rothenberg, Maria da Costa, Craig Fischer and M. Perwaiz Iqbal; Cancer Research 35, Aug. 1, 1975, 2033-2038, Computation of IC$_{50}$ Values IC$_{50}$ values were obtained from radioligand displacement or guanidine flux inhibition curves by plotting log$_{10}$ concentration vs bound ligand/guanidine uptake according the equation:—

$$y = Rmin + Rsp/\{1 + \exp[-n(x-C)]\}$$

where
y=bound (dpm)
x=log$_{10}$ compound concentration
Rmin=lower asymptote (i.e. 100% inhibition)
Rsp=upper asymptote-Rmin (i.e. specific binding)
n=slope (log$_e$)
and
C=IC$_{50}$ (i.e. concentration required to inhibit 50% of specific binding Hippocampal Slice Assay Neuroprotective efficacy was measured in 0.4 mm slices of rat hippocampus using the method described by Fowler and Li (1998)[1] except that Iodoacetate (400 μM)[2] was used as the metabolic insult. Compounds (usually 30 μM) were always directly compared with tetrodotoxin (1 μM)[3] for their ability to maintain slice concentrations of ATP following inhibition of glycolysis.

References:

1. Fowler J C, Li Y. Contributions of Na$^+$ flux and the anoxic depolarization to adenosine 5'-triphosphate levels in hypoxic/hypoglycemic rat hippocampal slices. Neuroscience 1998, 83, 717-722.

2. Reiner P B, Laycock A G, Doll C J. A pharmacological model of ischemia in the hippocampal slice. Neurosci Lett 1990; 119:175-8

3. Boening J A, Kass I S, Cottrell J E, Chambers G. The effect of blocking sodium influx on anoxic damage in the rat hippocampal slice. Neuroscience. 1989. vol 33 (2), 263-268.

Measurement of ATP and Protein

Individual slices were disrupted by ultra-sonication and the resulting homogenates centrifuged @ 10000×g for 5 min @ 4°. The supernatant was decanted into a fresh tube and any remaining supernatant removed by vacuum aspiration. The pellet was resuspended in 0.5 ml 0.1M KOH by ultra-sonication and the resulting suspensions warmed with gentle agitation @ 37° for 30 minutes.

Concentrations of ATP were measured in 6 μl of supernatant by mixing with Luciferase reagent (ATPLite from Perkin Elmer) and measuring subsequent luminescence in a 96-well plate Counter.

Protein concentration was measured using BCA™ protein assay (Pierce) with Bovine Serum albumin as reference standard.

ATP concentrations were expressed as nmoles/mg protein and neuroprotective indices (% protection) calculated by direct comparison with the effect of 1 μM TTX.

hERG:

Compounds were sent to MDS Pharma for measurement of their inhibition @ 10 μM concentration of the binding of [$^3$H]astemizole to HEK-293 cells expressing human recombinant hERG. Making the assumption that binding slopes would be 1.0° IC$_{50}$ values could be calculated (see above) for compounds exhibiting between 5% and 95% inhibition of binding.

L-type Calcium Channels

Compounds were sent to MDS Pharma for measurement of their inhibition @ 10 μM concentration of the binding of [$^3$H]nitrendipine to rat cerebral cortex membranes. Making the assumption that binding slopes would be 1.0° IC$_{50}$ values could be calculated (see above) for compounds exhibiting between 5% and 95% inhibition of binding.

Rat Microsome Stability

Compounds were sent to BioFocus for measurement of their stability @ 1 μM concentration following incubation with rat liver microsomes for 40 minutes @ 37°.

The screening data obtained in respect of representative compounds of the invention points to the suitability of compounds of general formula (VI)) for treatment of disorders in mammals that are susceptible to sodium channel blockers and antifolates, and particularly disorders such epilepsy, multiple sclerosis, glaucoma and uevitis, cerebral traumas and cerebral ischaemias, stroke, head injury, spinal cord injury, surgical trauma, neurodegenerative disorders, motorneurone disease, Alzheimer's disease, Parkinson's disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

The data from the procedures is set out in the Table below:

| Compound No. | Structure | Nach ([$^3$H]BTX-B) (extrapolated IC50 μM) | DHFR (% inhibition @ 125 μm) |
|---|---|---|---|
| CEN-230 | 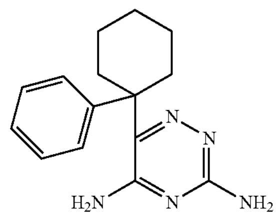 [SMILES: Nc1nnc(C2(c3ccccc3)CCCCC2)c(N)n1] | 23 | 0 |
| CEN-231 | 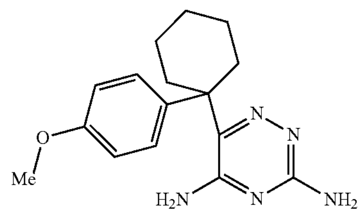 [SMILES: COc1ccc(C2(c3nnc(N)nc3N)CCCCC2)cc1] | 1 | ND |
| CEN-232 | 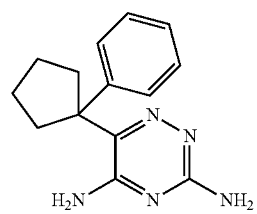 [SMILES: Nc1nnc(C2(c3ccccc3)CCCC2)c(N)n1] | 5 | 100 |
| CEN-234 | 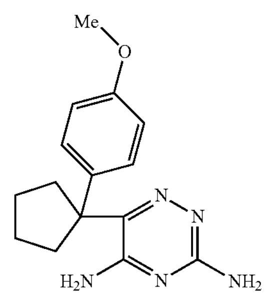 [SMILES: COc1ccc(C2(c3nnc(N)nc3N)CCCC2)cc1] | 3 | 22 |
| CEN-235 | 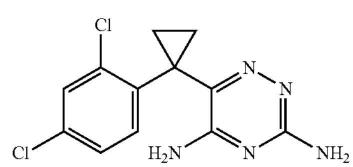 [SMILES: Nc1nnc(C2(c3ccc(Cl)cc3Cl)CC2)c(N)n1] | 8 | 63 |
| CEN-236 | 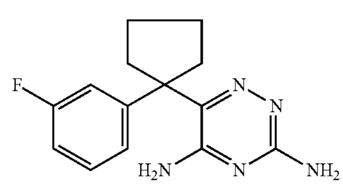 [SMILES: Nc1nnc(C2(c3cccc(F)c3)CCCC2)c(N)n1] | 4 | 14 |

| Compound No. | Structure | Nach ([³H]BTX-B) (extrapolated IC50 μM) | DHFR (% inhibition @ 125 μm) |
|---|---|---|---|
| CEN-237 | 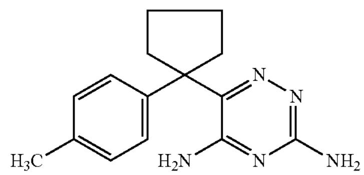 [SMILES: Cc1ccc(C2(c3nnc(N)nc3N)CCCC2)cc1] | <0.5 | 70 |
| CEN-238 | 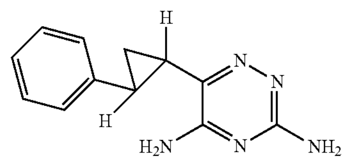 [SMILES: Nc1nnc(C2CC2c2ccccc2)c(N)n1] | >190 | ND |
| CEN-239 | 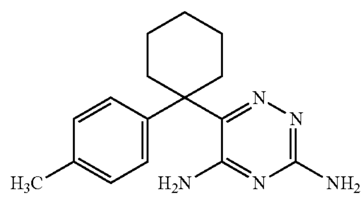 [SMILES: Cc1ccc(C2(c3nnc(N)nc3N)CCCCC2)cc1] | <0.5 | 73 |
| CEN-240 | 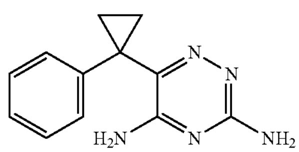 [SMILES: Nc1nnc(C2(c3ccccc3)CC2)c(N)n1] | >190 and 31.7 | 8 |
| CEN-241 | 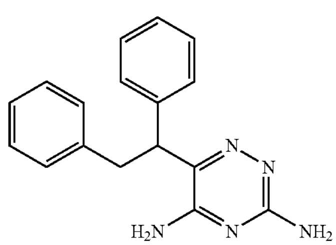 [SMILES: Nc1nnc(C(Cc2ccccc2)c2ccccc2)c(N)n1] | <0.5 and 1.5 | 90 |
| CEN-244 | 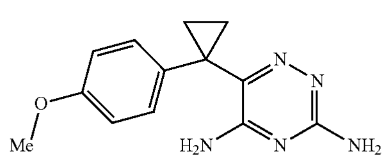 | 115 | 0 |
| CEN-245 | 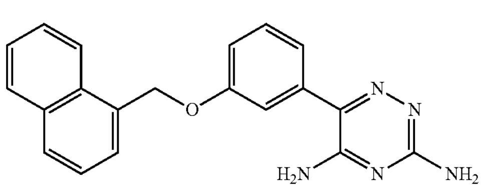 [SMILES: Nc1nnc(-c2cccc(OCc3cccc4ccccc34)c2)c(N)n1] | 57 | 55 |

| Compound No. | Structure | Nach ([³H]BTX-B) (extrapolated IC50 μM) | DHFR (% inhibition @ 125 μm) |
|---|---|---|---|
| CEN-247 | 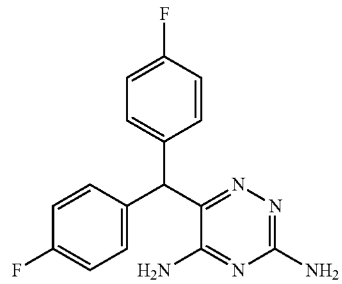 [SMILES: Nc1nnc(C(c2ccc(F)cc2)c2ccc(F)cc2)c(N)n1] | 9 | 0 |

(CEN-001) Lamotrigine result using same enzyme prep @ 125 microMolar gave 26% inhibition

The invention claimed is:

1. A compound of formula (I)

(I)

wherein:
R1 is hydrogen or a substituent group;
R2 is amino or a substituent group;
N* is amino when $R_1$ is hydrogen or =NH when $R_1$ is a substituent group;
R3 and R4 are both carbocyclic, heterocyclic or alkyl groups and may be same or different; and
R5 is hydrogen, alkyl or a cyclic aryl group, with the proviso that: when R3 and R4 are both alkyl they are linked to form a cycloalkyl group, and R5 is an aromatic or cyclic aliphatic group; and when R3 and R4 are both carbocyclic or heterocyclic groups, R5 is hydrogen, an alkyl group or an aromatic group;
or a salt thereof.

2. A compound as claimed in claim 1 wherein R3 and R4 are aromatic carbocycles or aromatic heterocycles and R5 is hydrogen.

3. A compound as claimed in claim 1 wherein R3 and R4 are both alkyl and are linked to form a cyclopropyl, cyclobutyl, cyclopentyl or cyclohexyl group.

4. A compound as claimed in claim 1 wherein alkyl groups for R3, R4 or R5 are selected from methyl, ethyl, propyl and butyl, optionally substituted by halogen or alkoxy groups.

5. A compound as claimed in claim 1 wherein at least one of R3, R4 and R5 is a carbocyclic ring system optionally substituted by one or more halogens or alkoxy groups.

6. A compound as claimed in claim 1 wherein at least one of R3, R4 and R5 is a heterocyclic ring system with one or more oxygen or sulphur or nitrogen atoms.

7. A compound as claimed in claim 6 wherein R3=R4.

8. A compound as claimed in claim 6 wherein the heterocyclic ring system is selected from
i) thienyl and benzothienyl, optionally substituted by halogen, alkyl or alkoxy;
ii) furyl, phenylfuryl and benzopyranyl, optionally substituted by halogen, alkyl or alkoxy; and/or
iii) pyridyl, indolyl, quinolyl, isoquinolyl, optionally substituted, for example by halogen, alkyl or alkoxy, and optionally N-substituted by alkyl, phenoxy or phenylthio.

9. A compound as claimed in claim 1 wherein R1 is carboxamido, $C_{1-10}$ alkyl, $C_{2-10}$ alkenyl, $C_{1-3}$ alkyl-aryl, $C_{1-3}$ alkyl-heterocyclyl, or $C_{3-10}$ cycloalkyl, optionally substituted by hydroxy, halogen, carboxamido, halo $C_{1-6}$ alkyl, $C_{1-6}$ alkyl or $C_{1-6}$ alkoxy.

10. A compound as claimed in claim 9 wherein R1 is a $C_{1-6}$ alkyl group, optionally substituted by hydroxy or halogen.

11. A compound as claimed in claim 9 wherein R1 is $C_{1-10}$ halo-alkyl.

12. A compound as claimed in claim 11 wherein R1 is methyl, ethyl, i-propyl, n-propyl, i-butyl or n-butyl, substituted by one or more halogens.

13. A compound as claimed in claim 11 wherein R1 is di- or tri-halo-substituted.

14. A compound as claimed in claim 9 wherein R1 is an unsubstituted $C_{2-6}$ alkenyl group.

15. A compound as claimed claim 9 wherein R1 is cyclohexyl, optionally substituted by one or more halogen, haloalkyl or alkoxy groups.

16. A compound as claimed in claim 9 wherein R1 is benzyl in which optionally the phenyl group is substituted by one or more halogen, haloalkyl or alkoxy groups.

17. A compound as claimed in claim 9 wherein R1 is piperidine-methyl, optionally N-substituted, or thienyl-methyl, or furyl-methyl.

18. A compound, wherein the compound is selected from:

CEN-230

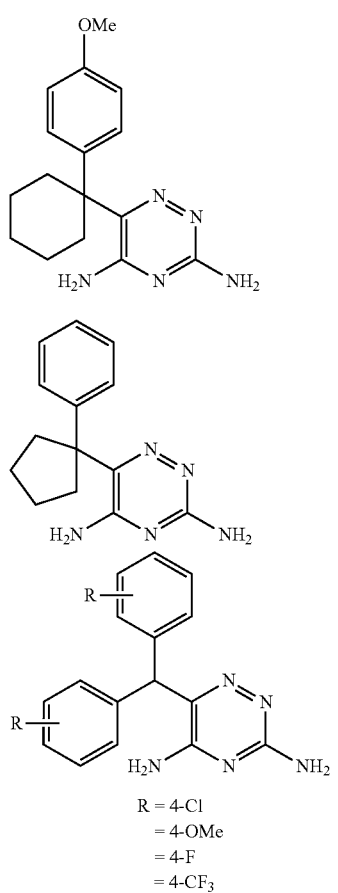
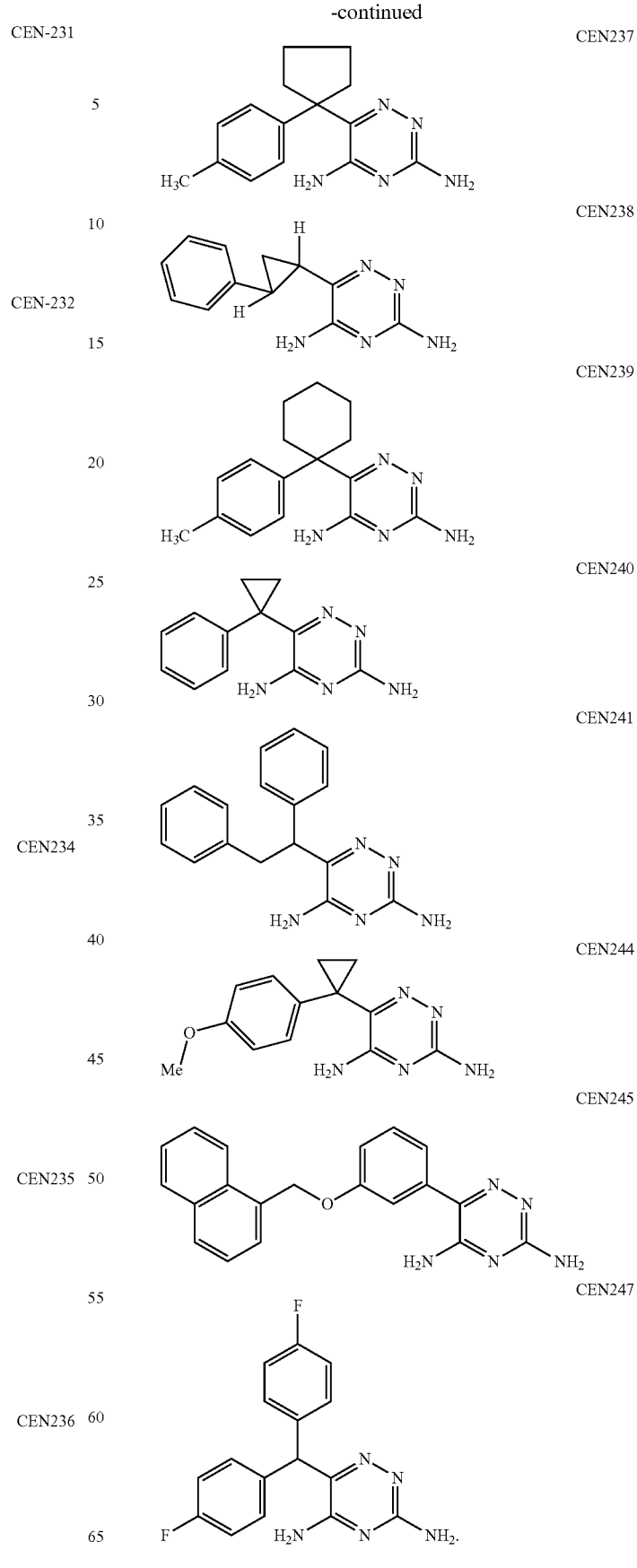

19. A pharmaceutical composition comprising a compound as claimed in claim 1 or a pharmaceutically acceptable salt thereof, in admixture with a pharmaceutically acceptable carrier.

20. A method of administering a therapeutically effective amount of a compound covered by formula (I) recited in claim 1 or a pharmaceutically acceptable salt thereof to a subject in need of treatment of epilepsy.

21. A compound as claimed in claim 5, wherein the ring system is phenyl.

22. A compound as claimed in claim 6, wherein the ring system is an aromatic ring system.

23. A compound as claimed in claim 6, wherein the ring system is a monocyclic or bicyclic ring system.

24. A method of administering a therapeutically effective amount of a compound covered by formula (I) recited in claim 1 or a pharmaceutically acceptable salt thereof to a subject in need of treatment of multiple sclerosis or neuropathic pain.

* * * * *